US006506895B2

(12) United States Patent
Guire et al.

(10) Patent No.: US 6,506,895 B2
(45) Date of Patent: *Jan. 14, 2003

(54) PHOTOACTIVATABLE NUCLEIC ACIDS

(75) Inventors: Patrick E. Guire, Eden Prairie, MN (US); Melvin J. Swanson, Carver, MN (US); Gary W. Opperman, St. Louis Park, MN (US)

(73) Assignee: SurModics, Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/028,806

(22) Filed: Feb. 24, 1998

(65) Prior Publication Data

US 2002/0086989 A1 Jul. 4, 2002

Related U.S. Application Data

(63) Continuation-in-part of application No. 08/916,913, filed on Aug. 15, 1997, now Pat. No. 6,121,027.

(51) Int. Cl.[7] .......................... C07H 21/00; C07H 21/04
(52) U.S. Cl. ............... 536/25.32; 536/25.3; 536/25.31; 536/25.34; 536/24.3; 536/24.31; 536/24.32
(58) Field of Search ............................. 536/25.3, 25.31, 536/25.32, 25.34, 24.3, 24.31, 24.32; 435/6

(56) References Cited

U.S. PATENT DOCUMENTS

| | | | |
|---|---|---|---|
| 4,629,623 A | 12/1986 | Balazs et al. | 424/78 |
| 4,722,906 A | 2/1988 | Guire | |
| 4,973,493 A | 11/1990 | Guire | 427/2 |
| 4,979,959 A | 12/1990 | Guire | |
| 5,217,492 A | 6/1993 | Guire et al. | |
| 5,263,992 A | 11/1993 | Guire | 623/66.1 |
| 5,512,329 A | 4/1996 | Guire et al. | |
| 5,563,056 A | 10/1996 | Swan et al. | |
| 5,580,697 A | 12/1996 | Keana et al. | 430/296 |
| 5,637,460 A | 6/1997 | Swan et al. | |
| 5,688,642 A | 11/1997 | Chrisey et al. | 435/6 |
| 5,714,360 A | 2/1998 | Swan et al. | |
| 5,718,726 A | 2/1998 | Amon et al. | 623/2 |
| 5,986,136 A | * 11/1999 | Maggio | 524/328 |
| 6,057,100 A | * 5/2000 | Heyneker | 435/6 |
| 6,121,027 A | * 9/2000 | Clapper et al. | 435/180 |

FOREIGN PATENT DOCUMENTS

| | | | |
|---|---|---|---|
| EP | 0 761 244 A2 | 3/1997 | |
| WO | WO 91/08242 | 6/1991 | |
| WO | WO9210092 | 6/1992 | |
| WO | WO 93/09176 | 5/1993 | |
| WO | WO 93/16176 | 8/1993 | |
| WO | 9607695 | 3/1996 | |
| WO | 9608797 | 3/1996 | |
| WO | WO 96/36653 | 11/1996 | |
| WO | 9705344 | 2/1997 | |
| WO | PCT/US96/17645 | 5/1997 | C12N/11/00 |

OTHER PUBLICATIONS

Kinoshita, Y. et al., "Soft tissue reaction to collagen–immobilized porous polyethylene: subcutaneous implantation in rats for 20 wk", *Biomaterials*, vol. 14, No. 3, pp. 209–215 (1993).

Imanishi, Y. et al., "Block copolymerization of vinyl compounds by vinyl compounds by the terminal–group activation of poly($\alpha$–amino acids) and the characterization of block copolymers", *International Journal of Biological Macromolecules*, vol. 7, No. 2, pp. 89–99 (Apr. 1985).

Pease et al., "Light–generated oligonucleotide arrays for rapid DNA sequence analysis", Proceedings of the National Academy of Sciences of USA, vol. 91, May 1, 1994, pp. 5022–5026.

Guo et al., "Direct fluorescence analysis of genetic polymorphisms by hybridization with oligonucleotide arrays on glass supports", Nucleic Acids Research, vol. 22, No. 24, Dec. 11, 1994, pp. 5456–5465.

Stipp, D., "Gene Chip Breakthrough", *Fortune*, pp. 56–73, Mar. 31, 1997.

Borman, S., "DNA Chips Come of Age", *C& EN*, pp. 42–43, Dec. 9, 1996.

Lipshutz, R.J., et al., *BioTechniques* 19(3):442–447 (1995).

M. Pirrung, et al., "Proofing of Photolithographic DNA Synthesis with 3',5'–Dimethoxybenzoinloxycarbonyl–Protected Deoxynucleoside", *J. Org. Chem.*, 63:241–246 (1998).

"DNA Assay Developments: Surface Chemistry and Formats for Molecular Screening and Diagnostics", B. Sullivan, et al., Jun. 4, 1997.

Sastry, S.S., et al., *J. Biol. Chem.*, 272(6):3715–3723 (1997).

Travis, J., *Science News* 151:144–145 (1997).

Heller, R.A., et al., *Proc. Natl. Acad. Sci. USA*, 94:2150–2155 (1997).

Pieles, U. and U. Englisch, *Nucleic Acid Res.*, 17(1):285–299, 1989.

Takasugi, M., et al., *Proc. Natl. Acad. Sci. USA*, 88(13):5602–5606 (1991).

Goodchild, J., *Bioconjugate Chem.*, 1(3):165–187 (1990).

* cited by examiner

Primary Examiner—James O. Wilson
Assistant Examiner—Howard V. Owens, Jr.
(74) Attorney, Agent, or Firm—Merchant & Gould P.C.

(57) ABSTRACT

A photoactivatable nucleic acid derivative composition in which one or more photoreactive group(s) are bound to a natural or synthetic nucleic acid. The photoreactive groups can be bound to the nucleic acid before, during or after its formation, and can thereafter be activated in order to attach the nucleic acid to another molecule, e.g., to the surface of a solid support. Also described is a method of preparing such a composition, and a method of using such a composition to attach the nucleic acid to a another molecule, such as that provided by the surface of a substrate used to prepare a nucleic acid chip by photolithographic techniques.

21 Claims, No Drawings

PHOTOACTIVATABLE NUCLEIC ACIDS

CROSS REFERENCE TO RELATED APPLICATIONS

This application is a continuation-in-part of U.S. patent application Ser. No. 08/916,913 for "Latent Reactive Polymers with Biologically Active Moieties", filed Aug. 15, 1997 now U.S. Pat. No. 6,121,027.

TECHNICAL FIELD

The present invention relates to the immobilization of nucleic acids. In another aspect, the invention relates to solid supports, such as oligonucleotide ("oligo") chips, incorporating such nucleic acids. In yet another aspect, the invention relates to photoreactive groups, to molecules derivatized with such groups, and to the attachment of such molecules to support surfaces by the activation of such groups.

BACKGROUND OF THE INVENTION

The development of oligonucleotide ("oligo") probe arrays (more commonly known as "DNA chips" and "Gene Chip" (a registered trademark of Affymetrix, Inc.)) has made significant advances over the past few years, and is becoming the center of ever-increasing attention and heightened significance. See, for instance, Stipp, D., Fortune, p.56, Mar. 31, 1997. See also Borman, S., C&EN, p.42, Dec. 9, 1996, and Travis, J., Science News 151:144–145 (1997).

Typically, oligonucleotide probe arrays display specific oligonucleotide sequences at precise locations in an information rich format. In use, the hybridization pattern of a fluorescently labeled nucleic acid target is used to gain primary structure information for the target. This format can be applied to a broad range of nucleic acid sequence analysis problems including pathogen identification, forensic applications, monitoring mRNA expression and de novo sequencing. See, for instance, Lipshutz, R. J., et al., Bio-Techniques 19(3):442–447 (1995). Such arrays sometimes need to carry several tens of thousands, or even hundreds of thousands of individual probes. The chips also need to provide a broad range of sensitivities in order to detect sequences that may be expressed at levels anywhere from 1 to 10,000 copies per cell.

A variety of approaches have been developed for the fabrication and/or use of oligonucleotide probe arrays. See, for instance, Weaver, et al. (WO 92/10092) which describes a synthetic strategy for the creation of large scale chemical diversity on a solid-phase support. The system employs solid-phase chemistry, photolabile protecting groups and photolithography to achieve light-directed, spatially addressable, parallel chemical synthesis. Using the proper sequence of masks and chemical stepwise reactions, a defined set of oligos can be constructed, each in a predefined position on the surface of the array.

Using this technology, Affymetrix, Inc. (Santa Clara, Calif.), has developed large microarrays of oligonucleotides affixed to silicon wafers. In use, a researcher will extract mRNA from a cell or other biological source, convert it to cDNA and label the sample with a fluorescent probe. Sequences complimentary to the chip-bound probe will hybridize to the wafer and allow the researcher to determine their relative amounts by measuring the fluorescence of each spot. To date, for instance, researchers have been able to quantitatively measure the expression of more than 1000 human genes in this manner.

One drawback of the Affymetrix approach is the limitation of the oligo length that can be affixed to the surfaces. With present techniques, it is common that every addition step involved in the synthesis of oligos will result in some errors or truncated sequences. With oligo chips, however, it is not possible to perform conventional post-synthesis purification techniques (e.g., HPLC) in order to remove truncated sequences since the oligo sequences remain bound to the support.

Synteni (Palo Alto, Calif.) produces arrays of cDNA by applying polylysine to glass slides. Arrays of cDNAs are printed onto the coated slides followed by exposure to UV light, in order to crosslink the DNA with the polylysine. Unreacted polylysine is then blocked by reaction with succinic anhydride. These arrays, called "Gene Expression Microarrays" (GEM™) are used by labeling cDNA prepared from a normal cell with a fluorescent dye, then labeling cDNA from an abnormal cell with a fluorescent dye of a different color. These two labeled cDNA probes are simultaneously applied to the microarray, where they competitively bind to the arrayed cDNA molecules. This two color coding technique is used to identify the differences in gene expression between two cell samples. (Heller, R. A., et al., Proc. Natl. Acad. Sci. USA, 94:2150–2155 (1997)).

Others have described a photo-crosslinking compound known as psoralen. Psoralen is a polycyclic compound having a planar configuration that intercalates within nucleic acid helices. When irradiated with UV light, the intercalated psoralen induces the formation of inter-strand linkages within the DNA molecule. Oligonucleotides derivatized at the 5'-terminus with psoralen have been used to crosslink double-stranded (Pieles, U. and U. Englisch, Nucleic Acid Res., 17(1):285–299, 1989), or triplex nucleic acids in solution (Takasugi, M., et al., Proc. Natl. Acad. Sci. USA, 88(13):5602–5606 (1991)). Psoralen derivatives have also been used to crosslink DNA-binding proteins to DNA (Sastry, S. S., et al., J. Biol. Chem., 272(6):3715–3723 (1997)).

In a different application, psoralen derivatives have been used to covalently bond functional groups to the surface of solid supports such as polystyrene. Those functional groups, in turn, are then used to thermochemically attach compounds to the support surface (Goodchild, J., Bioconjugate Chem., 1(3):165–187 (1990)). Currently, Nalge Nunc International uses this process to produce microplates that provide amine-functionalized surfaces for the thermochemical attachment of molecules such as nucleic acids. See, e.g., "DNA Assay Developments: Surface Chemistry and Formats for Molecular Screening and Diagnostics", B. Sullivan, et al., Jun. 4, 1997, Nalge Nunc International Corporation product literature.

On a separate subject, the assignee of the present invention has previously described a variety of applications for the use of photochemistry, and in particular, photoreactive groups, e.g., for attaching polymers and other molecules to support surfaces. See, for instance, U.S. Pat. Nos. 4,722,906, 4,979,959, 5,217,492, 5,512,329, 5,563,056, 5,637,460, and 5,714,360 and International Patent Application Nos. PCT/US96/08797 (Virus Inactivating Coatings), PCT/US96/07695 (Capillary Endothelialization), and PCT/US97/05344 (Chain Transfer Agents).

To the best of Applicant's knowledge, however, the art does not teach, nor are there commercial products that involve, the activation of pendent photoreactive groups to attach nucleic acids to surfaces in a specific and controllable fashion. The attachment of a nucleic acid to a surface by irradiation would appear to be susceptible to radiation-induced damage, and would be inherently nonspecific. See, for instance, M. Pirrung, et al., *J. Org. Chem.*, 63:241–246 (1998), which states that "irradiation [during deprotection] with wavelengths<340 nm should be avoided . . . based on the potential photochemical damage to the DNA."

In spite of the developments to date, there remains a need for methods and reagents that improve the immobilization of nucleic acids onto a variety of support materials, e.g., in order to form oligonucleotide probe arrays.

SUMMARY OF THE INVENTION

The present invention provides a composition comprising a photoactivatable nucleic acid derivative, in the form of a nucleic acid having one or more photoreactive groups bound thereto. The photoreactive group(s) are preferably covalently bound, directly or indirectly, at one or more points along the nucleic acid. Such groups can be activated in order to attach the nucleic acid to the surface of a solid support, such as the surface of a chip. A photoreactive group of this invention is separate and distinct from whatever group or bonds within the nucleic acid may be susceptible to radiation. In turn, the photogroup provides a derivatized nucleic acid that can be selectively and specifically activated in order to attach the nucleic acid to a support, and in a manner that substantially retains its desired chemical or biological function.

As used herein, unless otherwise indicated, a "photoreactive compound" is a compound that is, or contains, one or more "photoreactive groups", and can be used to derivatize a nucleic acid in order to form a "photoactivatable nucleic acid derivative" having one or more photoreactive groups, directly or indirectly, covalently bound and pendent thereto. By "direct", its inflections, it is meant that the photoreactive compound is attached directly to the nucleic acid, whereas the "indirect", and its inflections, will refer to the attachment of a photoreactive compound and nucleic acid to a common structure, such as a synthetic or natural polymer.

Applicants have discovered that photoreactive groups can be used to form derivatized nuleic acids, which in turn can be activated in order to attach the nucleic acids to the surface of a support in a manner that does not detrimentally affect the use of the immobilized nucleic acid for its intended purpose.

The present invention further provides a method of preparing such a composition, for instance, by derivatizing a nucleic acid with one or more photoreactive groups. The resultant photo-derivatized nucleic acid (e.g., oligonucleotide) can be covalently immobilized by the application of suitable irradiation, and usually without the need for surface pretreatment, to a variety of polymeric substrate surfaces. Thus, in one embodiment, the present invention provides a method that includes both the thermochemical attachment of one or more photoreactive groups to a nucleic acid and the photochemical immobilization of that nucleic acid derivative upon a substrate surface. This invention is particularly valuable for the fabrication of arrays of immobilized nucleic acids, e.g., by the use of printing or photolithographic techniques.

A particular advantage of covalently bonding nucleic acids onto surfaces, in a preferred embodiment described herein, is that the regions between the spots of immobilized nucleic acids remain hydrophobic, thereby providing clear separation between spots. There are also clear advantages of stable covalent bonds over adsorption. Stable bonds are important in applications where stringent hybridizations are needed or when amplification techniques, such as polymerase chain reaction (PCR), are used that involve thermocycling or where multiple probing is needed.

In another aspect, the invention provides a method of fabricating a nucleic acid probe array by the use of a photoactivatable nucleic acid composition as described herein. In yet another aspect, the invention provides a nucleic acid probe array fabricated by the use of one or more photoactivatable nucleic acid derivatives.

The photoactivatable nucleic acid derivative can take any suitable form, e.g., in the form of a single nucleic acid having one or more photogroups. In use, the photoactivatable nucleic acid derivatives of this invention provide a unique and convenient method for fabricating a nucleic acid probe array or for other methods involving nucleic acid immobilization.

DETAILED DESCRIPTION

Photoactivatable nucleic acid derivatives of the present invention can be provided in the form of one or more photoreactive groups bound (e.g., covalently attached directly or indirectly) to a nucleic acid. As used herein the term "nucleic acid" will include any of the group of polynucleotide compounds having bases derived from purine and from pyrimidine. Nucleic acids of particular use in the present invention include generally short, synthetic sequences more commonly known as oligonucleotides. The nucleic acid can be in any suitable form, e.g., single stranded, double stranded, or as a nucleoprotein. Examples of suitable nucleic acids include synthesized and/or natural molecules of deoxyribonucleic acid (DNA) (such as complementary DNA (cDNA)), ribonucleic acid (RNA), and peptide nucleic acid (PNA). PNA is a DNA mimic in which the native sugar phosphate DNA backbone has been replaced by a polypeptide. This substitution is said to increase the stability of the molecule, as well as improve both affinity and specificity.

One or more photogroups can be bound (e.g., directly) to the nucleic acid in any suitable fashion, e.g., by synthesizing an oligonucleotide, or derivatizing a natural or previously synthesized oligonucleotide, in such a manner as to provide a photogroup at the 3'-terminus, at the 5'-terminus, along the length of the oligonucleotide itself (e.g., pendent to an intermediate nucleotide or spacer within the nucleic acid), or any combination thereof.

The oligonucleotide component of a photoactivatable oligonucleotide composition can be synthesized using any suitable approach, including methods based on the phosphodiester chemistry and more recently, on solid-phase phosphoramidite techniques. See, generally, T. Brown and D. Brown, "Modem Machine-Aided Methods of Oligonucleotide Synthesis", Chapter 1, pp. 1–24 in *Oligonucleotides and Analogues, A Practical Approach*, F. Eckstein, ed., IRL Press (1991), the disclosure of which is incorporated herein by reference.

The stepwise synthesis of oligonucleotides generally involves the formation of successive diester bonds between 5'-hydroxyl groups of bound nucleotide derivatives and the 3'-hydroxyl groups of a succession of free nucleotide derivatives. The synthetic process typically begins with the attachment of a nucleotide derivative at its 3'-terminus by means of a linker arm to a solid support, such as silica gel or beads of borosilicate glass packed in a column. The ability to activate one group on the free nucleotide derivative requires that other potentially active groups elsewhere in the reaction mixture be "protected" by reversible chemical modifications. The reactive nucleotide derivative is a free monomer in which the 3'-phosphate group has been substituted, e.g., by dialkylphosphoramidite, which upon activation reacts with the free 5'-hydroxyl group of the bound nucleotide to yield a phosphite triester. The phosphite triester is then oxidized to a stable phosphotriester before the next synthesis step.

The 3'-hydroxyl of the immobilized reactant is protected by virtue of its attachment to the support and the 5'-hydroxyl of the free monomer can be protected by a dimethoxytrityl (DMT) group in order to prevent self-polymerization. A 2-cyanoethyl group is usually used to protect the hydroxyl of the 3'-phosphate. Additionally, the reactive groups on the individual bases are also protected. A variety of chemical techniques have been developed for the protection of the nucleotide exocyclic amino groups. The use of N-acetyl protecting groups to prepare N-acetylated deoxynucleotides has found wide acceptance for such purposes.

After each reaction, excess reagents are washed off the columns, any unreacted 5'-hydroxyl groups are blocked or "capped" using acetic anhydride, and the 5'-DMT group is removed using dichloroacetic acid to allow the extended bound oligomer to react with another activated monomer in the next round of synthesis.

Finally, the fully assembled oligonucleotide is cleaved from the solid support and deprotected, to be purified by HPLC or some other method. The useful reagents and conditions for cleavage depend on the nature of the linkage. With ester linkages, as are commonly provided by linkage via succinyl groups, cleavage can occur at the same time as deprotection of the bases using concentrated aqueous ammonium hydroxide.

A composition of the present invention can be prepared by modifying nucleic acids using techniques within the skill of those in the art, given the present teaching. A review of methods for modifying nucleic acids is contained in *Bioconjugate Chem.*, 3(1):165–186 (1990), the disclosure of which is incorporated herein by reference. Such methods include modifications introduced during chemical modifications of native or synthetic DNA, oligonucleotide synthesis, and enzymatic modifications.

In one embodiment of the present invention, nucleic acids, either natural or synthetic, can be derivatized with photoreactive groups randomly attached along the backbone or at either their 3'- or 5'- ends. For example, the bases present on the nucleotides making up the nucleic acid possess numerous reactive groups that can be derivatized using a heterobifunctional photoreactive compound having both a photoreactive group and a thermochemically reactive group suitable for covalent coupling to the bases. This approach will typically result in a relatively nonselective derivatization of the nucleic acid, both in terms of the location along the backbone as well as the number of photogroups per molecule.

In an alternative and more selective embodiment, a method of this invention can include the post-synthetic photoderivatization of an oligonucleootide which has had chemically reactive groups incorporated at specific sites during the synthesis, e.g. along the backbone or at either its 3'- or 5'- ends. For example, commercially available reagents or solid supports are available which permit the incorporation of amine groups at any of these locations in the oligonucleotide. These amine groups are then combined with a photoreactive compound having a photogroup and an N-oxysuccinimide ester (NOS), resulting in formation of an amide bond between the photogroup and the oligonucleotide. Those skilled in the art, given the present description, will appreciate the manner in which a variety of other reactions between electrophilic and nucleophilic species can provide similar coupling techniques. For example, the reaction between carboxylic acid chlorides with amines, or maleimide groups with sulfhydryl groups can be used to provide photoactivatible nucleic acid derivatives as well.

In another embodiment, one or more of the nucleotide building blocks typically used in oligo synthesis can themselves be derivatized with a reagent containing a photoreactive group by attachment of the reagent to one of the reactive functionalities present on the base residue of the nucleotide. The resulting derivatized nucleotide reagent can be used in an automated synthesizer, under conventional reaction conditions, in order to incorporate the photogroup at designated points along the chain or at either end of the oligonucleotide. In addition, commercially available non-nucleotide reagents, used for incorporation of chemically reactive groups as described above, can be reacted with the photoreactive compound to incorporate the photoreactive group, after which they can be used in the automated synthesizer to prepare the photoactivatible nucleic acids.

A variety of reagents are available for use in modifying nucleic acids, including those available under the trade name "Biotin-Chem-Link" from Boehringer Mannheim (Indianapolis, Ind.). This cis-platinum reagent will bind to the N7 position of guanosine and adenosine bases. In a similar fashion, a photoreactive compound containing a cis-platinum moiety can be synthesized for use in photo-derivatizing nucleic acids.

In another aspect, photoderivatized nucleotides can be synthesized and incorporated into nucleic acids using enzymatic techniques. For instance, a variety of reagents are available that can be used to label nucleic acids with biotin, fluorescein and digoxigenin (DIG). A nucleic acid can be labeled with a photoactivatable dideoxyribonucleotide or deoxyribonucleotide, using a terminal transferase, in order to provide either single or multiple photogroups, respectively, at the 3'-end of the nucleic acid.

Boehringer-Mannheim also sells a DIG-labeling kit called "DIG-High Prime" for random primed labeling of DNA with DIG-11-UTP. "Biotin High Prime" and "Fluorescein-High-Prime" products are also available. In a similar fashion, DNA can be random-primed labeled with a photoactivatable deoxyribonucleotide using the Klenow enzyme, as will become apparent to those skilled in the art.

DNA Polymerase I enzyme is commonly used for nick translation of DNA. By including photoactivatable deoxyribonucleotides in the mixture of deoxynucleotide triphosphates ("dNTPs") the resulting polymerized product will contain one or more photoreactive groups along its length. Also, during Polymerase Chain Reaction (PCR) a photoactivatable deoxyribonucleotide can be included in the mixture of dNTPs for the labeling of amplification products. It is also possible to incorporate a photoribonucleotide into RNA, e.g., by the use of an RNA polymerase (e.g., SP6 or T7) and standard transcription protocols.

In a further embodiment of the invention, oligos can be derivatized with photoreactive groups by forming or attaching the intact oligo as a ligand along the backbone of a polymer that provides one or more photoreactive groups along its length, e.g., as described in co-pending U.S. patent application Ser. No. 08/916,913 for "Latent Reactive Polymers with Biologically Active Moieties", filed Aug. 15, 1997, the disclosure of which is incorporated herein by reference. A number of approaches can be used for the preparation of such a polymeric photo-oligo reagent. In one embodiment, the oligo can be prepared in monomer form by covalent attachment of a polymerizable vinyl group such as acryloyl to the oligo, either at the ends or along the backbone. This can be accomplished by reaction of acryloyl chloride with an amine derivatized oligo. These oligo monomers can then be copolymerized with a photoderivatized monomer along with other comonomers such as acrylamide or vinylpyrrolidone. The resulting polymer provides photogroups and oligos randomly attached along the backbone of the polymer. Alternatively, the polymer can be prepared with the photoreactive group at one end of the polymer by use of a chain transfer reagent having one or more photoreactive groups as part of the structure.

In yet a further embodiment, a photoreactive polymer (e.g., a preformed synthetic or naturally occuring polymer that itself is provided with photogroups) can be derivatized with oligos in order to form a composition of the present invention. In this approach, a polymer can be prepared, or modified, in order to have chemically reactive groups located along the backbone of the polymer, each of which is capable of reacting with appropriately substituted oligos. For example, polymers possessing activated groups such as NOS esters can be reacted with oligos containing amine functionality resulting in covalent attachment of the oligo to the polymer backbone through an amide bond. The polymeric portion itself can be derivatized with photogroups, either before, during or after its bonding to the oligo. For instance, a photoderivatized polymer can be prepared by polymerizing monomers that include photoderivatized monomers, or one or more photogroup can be added to the formed polymer in a manner similar to that described above with respect to oligos. Alternatively, polymers can be prepared having terminal photoreactive groups by the use of a chain transfer reagent having a photogroup as part of its structure. The oligo would then be added to the reactive groups in a second step.

The polymer backbone can be either synthetic or naturally occurring, and is preferably a synthetic polymer selected from the group consisting of oligomers, homopolymers, and copolymers resulting from addition or condensation polymerization. Naturally occurring polymers, such as polysaccharides and polypeptides, can be used as well. Preferred backbones are biologically inert, in that they do not provide a biological function that is inconsistent with, or detrimental to, their use in the manner described. Such polymer backbones can include acrylics such as those polymerized from hydroxyethyl acrylate, hydroxyethyl methacrylate, glyceryl acrylate, glyceryl methacrylate, acrylic acid, methacrylic acid, acrylamide and methacrylamide; vinyls such as polyvinyl pyrrolidone and polyvinyl alcohol; nylons such as polycaprolactam, polylauryl lactam, polyhexamethylene adipamide and polyhexamethylene dodecanediamide; polyurethanes; polyethers such as polyethylene oxide, polypropylene oxide, and polybutylene oxide; and biodegradable polymers such as polylactic acid, polyglycolic acid, polydioxanone, polyanhydrides, and polyorthoesters.

Photoreactive Groups

A preferred composition of this invention includes one or more pendent latent reactive (preferably photoreactive) groups covalently attached, directly or indirectly, to a nucleic acid. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10- position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene.

Upon activation of the photoreactive groups, the reagent molecules are covalently bound to each other and/or to the material surface by covalent bonds through residues of the photoreactive groups. Exemplary photoreactive groups, and their residues upon activation, are shown as follows.

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—SO$_2$—NH—R' |
| phosphoryl azides | phosphoramide | (RO)$_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

The photoactivatable nucleic acids of the invention can be applied to any surface having carbon-hydrogen bonds, with which the photoreactive groups can react to immobilize the nucleic acids to surfaces. Examples of appropriate substrates include, but are not limited to, polypropylene, polystyrene, poly(vinyl chloride), polycarbonate, poly(methyl methacrylate), parylene and any of the numerous organosilanes used to pretreat glass or other inorganic surfaces. The photoactivatable nucleic acids can be printed onto surfaces in arrays, then photoactivated by uniform illumination to immobilize them to the surface in specific patterns. They can also be sequentially applied uniformly to the surface, then photoactivated by illumination through a series of masks to immobilize specific sequences in specific regions. Thus, multiple sequential applications of specific photoderivatized nucleic acids with multiple illuminations through different masks and careful washing to remove uncoupled photonucleic acids after each photocoupling step can be used to prepare arrays of immobilized nucleic acids. The photoactivatable nucleic acids can also be uniformly immobilized onto surfaces by application and photoimmobilization.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Preparation of a Benzophenone Substituted Oligonucleotide (a) Preparation of N-Succinimidyl 6-(4-Benzoylbenzamido) hexanoate (BBA-EAC-NOS)

4-Benzoylbenzoyl chloride, 60 g (0.246 moles), prepared as described in Example 3(a), was dissolved in 900 ml of chloroform. The 6-aminohexanoic acid, 33.8 g (0.258 moles), was dissolved in 750 ml of 1 N NaOH and the acid chloride solution was added with stirring. The mixture was stirred vigorously to generate an emulsion for 45 minutes at room temperature. The product was then acidified with 75 ml of 12 N HCl and extracted with 3×500 ml of chloroform. The combined extracts were dried over sodium sulfate, filtered, and evaporated under reduced pressure. The 6-(4-benzoylbenzamido)hexanoic acid was recrystallized from toluene/ethyl acetate (3/1 by volume) to give 77.19 g (93% yield) of product, m.p. 106.5–109.5° C.

The 6-(4-benzoylbenzamido)hexanoic acid, 60 g (0.177 mmoles), was added to a dry flask and dissolved in 1200 ml of dry 1,4-dioxane. N-Hydroxysuccinimide, 21.4 g (0.186 moles) was added followed by 41.9 g (0.203 moles) of 1,3-dicyclohexylcarbodiimide and the mixture was stirred overnight at room temperature under a drying tube to protect the reaction from moisture. After filtration to remove the 1,3-dicyclohexylurea, the solvent was removed under reduced pressure and the resulting oil was diluted with 300 ml of dioxane. Any remaining solids which formed were removed by filtration and after removal of solvent, the BBA-EAC-NOS was recrystallized twice from ethanol to give 60.31 g of a white solid, m.p. 123–126° C.

(b) Photoderivatization of an Amino-Modified Oligonucleotide

A 30-base oligomer (-mer) probe (Sequence (or "Seq") 1), synthesized with a 5'-amino-modifier containing a C-12 spacer (amine-Sequence 1), was custom made at Midland Certified Reagent Company (Midland, Tex.). Oligonucleotide amine-Sequence 1, 100 μg (10 nmole, 39.4 μl of 2.54 mg/ml stock in water) was mixed on a shaker in a microcentrifuge tube with 43.8 μg (100 nmole, 8.8 μl of 5 mg/ml stock in DMF) of BBA-EAC-NOS, prepared as described above in Example 1(a), and 4 μl of 1 M sodium bicarbonate buffer, pH 9. The reaction proceeded at room temperature for 3 hours. To remove unreacted BBA-EAC-NOS, the reaction was diluted with 148 μl phosphate buffered saline (PBS, 10 mM Na$_2$HPO$_4$, 150 mM NaCl, pH 7.2) and then loaded onto a NAP-5 column (Pharmacia Biotech, Uppsala, Sweden) according to the manufacturer's specifications. PBS was used to equilibrate the column and to elute the oligonucleotides off the column. The NAP-5 column, which contains Sephadex G-25 gel, separated oligonucleotides from the small molecular weight compound. A total of 3.1 A$_{260}$ units or 96 μg of benzophenone derivatized oligonucleotide Sequence 1 was recovered.

Example 2

Evaluation of the Benzophenone Substituted Oligonucleotide

Oligos amine-Sequence 1 and benzophenone-Sequence 1 at 5 pmole/0.1 ml per well were incubated in polypropylene (PP, Coming Costar, Cambridge, Mass.) microwell plates in the incubation buffer (50 mM phosphate buffer, pH 8.5, 1 mM EDTA, 15% Na$_2$SO$_4$) at room temperature overnight. Half of the plates were illuminated with a Dymax lamp (Model no. PC-2, Dymax Corporation, Torrington, Conn.) which contained a Heraeus bulb (W. C. Heraeus GmbH, Hanau, Federal Republic of Germany) and a cut-off filter that blocked out all light below 300 nm. The illumination duration was for 2 minutes at an intensity of 1–2 mW/cm$^2$ in the wavelength range of 330–340 nm. The remaining half of the plates that were not illuminated served as the adsorbed oligo controls. All of the plates were then washed with PBS containing 0.05% Tween 20 using a Microplate Auto Washer (Model EL 403H, Bio-Tek Instruments, Winooski, Vt.).

Hybridization was performed as described below using a complementary detection probe (Sequence 2) or the non-complementary oligonucleotide (Sequence 3). Both oligos were procured from the Mayo Clinic (Rochester, Minn.). The plates were blocked at 55° C. for 30 minutes with hybridization buffer consisting of 5X SSC (0.75 M NaCl, 0.075 M citrate, pH 7.0), 0.1% lauroylsarcosine, 1% casein, and 0.02% sodium dodecyl sulfate (SDS). When the detection probe was hybridized to the immobilized probe, an aliquot of 50 fmole of detection probe in 0.1 ml was added per well and incubated for 1 hour at 55° C. The plates were then washed with 2X SSC containing 0.1% SDS for 5 minutes at 55° C. The bound detection probe was assayed by adding 0.1 ml of a conjugate of streptavidin and horseradish peroxidase (SA-HRP, Pierce, Rockford, Ill.) at 0.5 μg/ml which was incubated for 30 minutes at 37° C. The plates were then washed with PBS/Tween, followed by the addition of peroxidase substrate ($H_2O_2$ and tetramethylbenzidine, Kirkegard and Perry Laboratories, Gaithersburg, Md.) and measurement at 655 nm, 20 minutes later, on a microwell plate reader (Model 3550, Bio-Rad Labs, Cambridge, Mass.).

The results listed in Table 1 show that the illuminated benzophenone-derivatized oligonucleotide provided a higher hybridization signal than the adsorbed oligonucleotide control. Conversely, there was no difference between the hybridization signals generated by the illuminated and the adsorbed non-derivatized oligonucleotides.

(b) Preparation of N-(3-Aminopropyl)methacrylamide Hydrochloride (APMA)

A solution of 1,3-diaminopropane, 1910 g (25.77 moles), in 1000 ml of $CH_2Cl_2$ was added to a 12 liter Morton flask and cooled on an ice bath. A solution of t-butyl phenyl carbonate, 1000 g (5.15 moles), in 250 ml of $CH_2Cl_2$ was then added dropwise at a rate which kept the reaction temperature below 15° C. Following the addition, the mixture was warmed to room temperature and stirred 2 hours. The reaction mixture was diluted with 900 ml of $CH_2Cl_2$ and 500 g of ice, followed by the slow addition of 2500 ml of 2.2 N NaOH. After testing to insure the solution was basic, the product was transferred to a separatory funnel and the organic layer was removed and set aside as extract #1. The aqueous was then extracted with 3×1250 ml of $CH_2Cl_2$, keeping each extraction as a separate fraction. The four organic extracts were then washed successively with a single 1250 ml portion of 0.6 N NaOH beginning with fraction #1 and proceeding through fraction #4. This wash procedure was repeated a second time with a fresh 1250 ml portion of 0.6 N NaOH. The organic extracts were then combined and dried over $Na_2SO_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of $CHCl_3$ was placed in a 12 liter Morton flask

TABLE 1

Hybridization Signals ($A_{655}$ ± standard deviation) from Amine-Sequence 1 and Benzophenone-Sequence 1 on PP Microwell Plates.

| | Adsorbed Control | | Illuminated | |
|---|---|---|---|---|
| | Complem. Det. Sequence 2 | Non-complem. Det. Sequence 3 | Complem. Det. Sequence 2 | Non-complem. Det. Sequence 3 |
| Amine-Sequence 1 | 0.289 ± 0.025 | 0.014 ± 0.005 | 0.250 ± 0.023 | 0.069 ± 0.005 |
| Benzophenone-Sequence 1 | 0.143 ± 0.034 | 0.008 ± 0.007 | 0.456 ± 0.027 | 0.026 ± 0.005 |

Example 3

Preparation and Evaluation of a Photopolymer Derivatized with Oligonucleotides (a) Preparation of 4-Benzoylbenzoyl Chloride (BBA-Cl)

4-Benzoylbenzoic acid (BBA), 1 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from toluene/hexane (¼ by volume) to give 988 g (91% yield) after drying in a vacuum oven. Product melting point was 92–94° C. Nuclear magnetic resonance (NMR) analysis at 80 MHz ($^1$H NMR ($CDCl_3$)) was consistent with the desired product: aromatic protons 7.20–8.25 (m, 9H). All chemical shift values are in ppm downfield from a tetramethylsilane internal standard. The final compound was stored for use in the preparation of a monomer used in the synthesis of photoactivatable polymers as described, for instance, in Example 3(c) or for heterobifunctional compounds as described, for instance, in Example 1(a).

equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of $CHCl_3$. The rate of addition was controlled to keep the reaction temperature below 10° C. at all times. After the addition was complete, the ice bath was removed and the mixture was left to stir overnight. The product was diluted with 2400 ml of water and transferred to a separatory funnel. After thorough mixing, the aqueous layer was removed and the organic layer was washed with 2400 ml of 2 N NaOH, insuring that the aqueous layer was basic. The organic layer was then dried over $Na_2SO_4$ and filtered to remove drying agent. A portion of the $CHCl_3$ solvent was removed under reduced pressure until the combined weight of the product and solvent was approximately 3000 g. The desired product was then precipitated by slow addition of 11 liters of hexane to the stirred $CHCl_3$ solution, followed by overnight storage at 4° C. The product was isolated by filtration and the solid was rinsed twice with a solvent combination of 900 ml of hexane and 150 ml of $CHCl_3$. Thorough drying of the solid gave 900 g of N-[N'-(t-butyloxycarbonyl)-3-aminopropyl]-methacrylamide, m.p. 85.8° C. by DSC. Analysis on an NMR spectrometer was consistent with the desired product: $^1$H NMR ($CDCl_3$) amide NH's 6.30–6.80, 4.55–5.10 (m, 2H), vinyl protons 5.65, 5.20 (m, 2H), methylenes adjacent to N 2.90–3.45 (m, 4H), methyl 1.95 (m, 3H), remaining methylene 1.50–1.90 (m, 2H), and t-butyl 1.40 (s, 9H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5 M by titration with 1 N NaOH using phenolphthalein as an indicator. The N-[N'-(t-butyloxycarbonyl)-3-aminopropyl] methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5 M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. The N-(3-aminopropyl) methacrylamide hydrochloride was isolated by filtration and was dried to constant weight, giving a yield of 630 g with a melting point of 124.7° C. by DSC. Analysis on an NMR spectrometer was consistent with the desired product: $^1$H NMR (D$_2$O) vinyl protons 5.60, 5.30 (m, 2H), methylene adjacent to amide N 3.30 (t, 2H), methylene adjacent to amine N 2.95 (t, 2H), methyl 1.90 (m, 3H), and remaining methylene 1.65–2.10 (m, 2H). The final compound was stored for use in the preparation of a monomer used in the synthesis of photoactivatable polymers as described, for instance, in Example 3(c).

(c) Preparation of N-[3-(4-Benzoylbenzamido)propyl] methacrylamide (BBA-APMA)

APMA, 120 g (0.672 moles), prepared according to the general method described in Example 3(b), was added to a dry 2 liter, three-neck round bottom flask equipped with an overhead stirrer. Phenothiazine, 23–25 mg, was added as an inhibitor, followed by 800 ml of chloroform. The suspension was cooled below 10° C. on an ice bath and 172.5 g (0.705 moles) of BBA-Cl, prepared according to the general method described in Example 3(a), were added as a solid. Triethylamine, 207 ml (1.485 moles), in 50 ml of chloroform was then added dropwise over a 1–1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from toluene/chloroform (4/1 by volume) using 23–25 mg of phenothiazine in each recrystallization to prevent polymerization. Typical yields of BBA-APMA were 90% with a melting point of 147–151° C. Analysis on an NMR spectrometer was consistent with the desired product: $^1$H NMR (CDCl$_3$) aromatic protons 7.20–7.95 (m, 9H), amide NH 6.55 (broad t, 1H), vinyl protons 5.65, 5.25 (m, 2H), methylenes adjacent to amide N's 3.20–3.60 (m, 4H), methyl 1.95 (s, 3H), and remaining methylene 1.50–2.00 (m, 2H). The final compound was stored for use in the synthesis of photoactivatable polymers as described, for instance, in Example 3(e).

(d) Preparation of N-Succinimidyl 6-Maleimidohexanoate (MAL-EAC-NOS)

A functionalized monomer was prepared in the following manner, and was used as described in Example 3(e) to introduce activated ester groups on the backbone of a polymer. 6-Aminohexanoic acid, 100 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2–50 ml of hexane. After drying, the typical yield of the (Z)-4-oxo-5-aza-2-undecendioic acid was 158–165 g (90–95%) with a melting point of 160–165° C. Analysis on an NMR spectrometer was consistent with the desired product: $^1$H NMR (DMSO-d$_6$) amide proton 8.65–9.05 (m, 1H), vinyl protons 6.10, 6.30 (d, 2H), methylene adjacent to nitrogen 2.85–3.25 (m, 2H), methylene adjacent to carbonyl 2.15 (t, 2H), and remaining methylenes 1.00–1.75 (m, 6H).

(Z)-4-Oxo-5-aza-2-undecendioic acid, 150 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to <60° C. and poured into a solution of 250 ml of 12 N HCl in 3 liters of water. The mixture was stirred 3 hours at room temperature and then was filtered through a Celite 545 pad to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from hexane/chloroform (2/1 by volume) to give typical yields of 76–83 g (55–60%) with a melting point of 81–85° C. Analysis on a NMR spectrometer was consistent with the desired product: $^1$H NMR (CDCl$_3$) maleimide protons 6.55 (s, 2H), methylene adjacent to nitrogen 3.40 (t, 2H), methylene adjacent to carbonyl 2.30 (t, 2H), and remaining methylenes 1.05–1.85 (m, 6H).

The 6-maleimidohexanoic acid, 20 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12 g (0.104 mol) of N-hydroxysuccinimide and 16 ml (0.114 mol) of triethylamine. After stirring overnight at room temperature, the product was washed with 4–100 ml of water and dried over sodium sulfate. Removal of solvent gave 24 g of product (82%) which was used without further purification. Analysis on an NMR spectrometer was consistent with the desired product: $^1$H NMR (CDCl$_3$) maleimide protons 6.60 (s, 2H), methylene adjacent to nitrogen 3.45 (t, 2H), succinimidyl protons 2.80 (s, 4H), methylene adjacent to carbonyl 2.55 (t, 2H), and remaining methylenes 1.15–2.00 (m, 6H). The final compound was stored for use in the synthesis of photoactivatable polymers as described, for instance, in Example 3(e).

(e) Preparation of a Copolymer of Acrylamide, BBA-APMA, and MAL-EAC-NOS

A photoactivatable copolymer of the present invention was prepared in the following manner. Acrylamide, 3.849 g (54.1 mmol), was dissolved in 52.9 ml of tetrahydrofuran (THF), followed by 0.213 g (0.61 mmol) of BBA-APMA, prepared according to the general method described in Example 3(c), 0.938 g (3.04 mmol) of MAL-EAC-NOS, prepared according to the general method described in Example 3(d), 0.053 ml (0.35 mmol) of N,N,N',N'-tetramethylethylenediamine (TEMED), and 0.142 g (0.86 mmol) of 2,2'-azobisisobutyronitrile (AIBN). The solution was deoxygenated with a helium sparge for 4 minutes, followed by an argon sparge for an additional 4 minutes. The sealed vessel was then heated overnight at 55° C. to complete the polymerization. The solid product was isolated by filtration and the filter cake was rinsed thoroughly with THF and $CHCl_3$. The product was dried in a vacuum oven at 30° C. to give 5.234 g of a white solid. NMR analysis (DMSO-$d_6$) confirmed the presence of the NOS group at 2.75 ppm and the photogroup load was determined to be 0.104 mmol BBA/g of polymer. MAL-EAC-NOS composed 5 mole % of the polymerizable monomers in this reaction.

(f) Preparation and Evaluation of a Photopolymer Derivatized with Oligonucleotides A 40-mer probe (Sequence 4) was synthesized with an amine modification as described for Sequence 1. Oligo amine-Sequence 4, 40 μg (15 μl of 2.67 mg/ml stock in water) was incubated with 80 μg (80 μl of 1 mg/ml freshly made in water) of a copolymer of acrylamide, BBA-APMA, and MAL-EAC-NOS, prepared as described in Example 3(e), and 305 μl of incubation buffer. The reaction mixture was stirred at room temperature for 2 hours. The resulting photopoly-Sequence 4 was used without further purification for immobilization.

Amine-Sequence 4 and photopoly-Sequence 4 at 10 pmole oligo/0.1 ml per well were incubated in PP and poly(vinyl chloride) microwell plates (PVC, Dynatech, Chantilly, Va.) in 50 mM phosphate buffer, pH 8.5, 1 mM EDTA for 1.5 hours at 37° C. The plates were illuminated or adsorbed as described in Example 2. Hybridization was performed as described in Example 2 using the complementary Sequence 3 detection oligonucleotide or non-complementary Sequence 2 oligonucleotide. The results from Table 2 indicate that the illuminated photopoly-oligonucleotide had 13- and 2-fold higher hybridization signals than the adsorbed control on PP and PVC surfaces, respectively. In contrast, illumination did not contribute to amine-Sequence 4 immobilization.

Example 4

Preparation of a Benzophenone Labeled Oligonucleotide by Direct Synthesis (a) Preparation of 4-Bromomethylbenzophenone (BMBP)

4-Methylbenzophenone, 750 g (3.82 moles), is added to a 5 liter Morton flask equipped with an overhead stirrer and dissolved in 2850 ml of benzene. The solution is then heated to reflux, followed by the dropwise addition of 610 g (3.82 moles) of bromine in 330 ml of benzene. The addition rate is approximately 1.5 ml/min and the flask is illuminated with a 90 watt (90 joule/sec) halogen spotlight to initiate the reaction. A timer is used with the lamp to provide a 10% duty cycle (on 5 seconds, off 40 seconds), followed in one hour by a 20% duty cycle (on 10 seconds, off 40 seconds). After cooling, the reaction mixture is washed with 10 g of sodium bisulfite in 100 ml of water, followed by washing with 3×200 ml of water. The product is dried over sodium sulfate and recrystallized twice from toluene/hexane (⅓ by volume). The final compound is stored for use in the preparation of a reagent suitable for derivatization of nucleic acids as described in Example 4(b).

(b) Preparation of 4-Benzoylbenzylether-$C_{12}$-phosphoramidite 1,12-Dodecanediol, 5 g (24.7 mmol), is dissolved in 50 ml of anhydrous THF in a dry flask under nitrogen. The sodium hydride, 0.494 g of a 60% dispersion in mineral oil (12.4 mmol), is added in portions over a five minute period. The resulting mixture is stirred at room temperature for one hour. BMBP, 3.40 g (12.4 mmol), prepared according to the general method described in Example 4(a), is added as a solid along with sodium iodide (0.185 g, 1.23 mmol) and tetra-n-butylammonium bromide (0.398 g, 1.23 mmol). The mixture is stirred at a gentle reflux for 24 hours. The reaction is then cooled, quenched with water, acidified with 5% HCl, and extracted with chloroform. The organic extracts are dried over sodium sulfate and the solvent is removed under vacuum. The product is purified on a silica gel flash chromatography column using chloroform to elute non-polar impurities, followed by elution of the product with chloroform:ethyl acetate (80/20 by volume). Pooling of appropriate fractions provides the desired compound after removal of solvent under reduced pressure.

The ether product from above, 0.100 g (0.252 mmol), is dissolved in chloroform under an argon atmosphere. N,N-Diisopropylethylamine, 0.130 g (1 mmol), is added and the

TABLE 2

Hybridization Signals ($A_{655}$ ± standard deviation) from Amine-Sequence 4 and Photopoly-Sequence 4 on PP and PVC Microwell Plates.

| | Adsorbed Control | | Illuminated | |
| --- | --- | --- | --- | --- |
| | Complem. Det. Sequence 3 | Non-complem. Det. Sequence 2 | Complem. Det. Sequence 3 | Non-complem. Det. Sequence 2 |
| PP plates | | | | |
| Amine-Sequence 4 | 0.034 ± 0.034 | 0.011 ± 0.001 | 0.001 ± 0.002 | 0.014 ± 0.005 |
| Photopoly-Sequence 4 | 0.099 ± 0.033 | 0.017 ± 0.015 | 1.356 ± 0.078 | 0.019 ± 0.021 |
| PVC plates | | | | |
| Amine-Sequence 4 | 0.153 ± 0.031 | 0.087 ± 0.025 | 0.001 ± 0.002 | 0.046 ± 0.006 |
| Photopoly Sequence 4 | 0.992 ± 0.071 | 0.097 ± 0.013 | 1.854 ± 0.042 | 0.087 ± 0.071 | temperature is adjusted to 0° C. using an ice bath. 2-Cyanoethyl diisopropylchlorophosphoramidite, 0.179 g (0.756 mmol), is then added in three equal portions over about 10 minutes. Stirring is continued for a total of three hours, after which time the reaction is quenched with 5% $NaHCO_3$ and diluted with 5 ml of chloroform. The organic layer is separated, dried over sodium sulfate, and evaporated to provide a residual oil. The crude product is purified on a silica gel flash chromatography column using a 5% methanol in chloroform solvent, followed by a ammonium hydroxide/methanol/chloroform (0.5/2.5/7 by volume) solvent system. The appropriate fractions are pooled and the solvent is removed to provide the desired product, suitable for derivatization of a nucleic acid.

(c) Preparation of a Benzophenone Labeled Oligonucleotide

A 30-mer oligonucleotide is synthesized on silica beads using standard oligonucleotide procedures and the beads are placed in a sealed vessel under an argon atmosphere. Solutions of 12.5 mg (22 μmol) of the phosphoramidite prepared in Example 4(b) in 0.5 ml of chloroform and 5 mg (71 μmol) of tetrazole in 0.5 ml of acetonitrile are then added. The mixture is gently agitated for 1 hour, followed by the removal of the supernatant. The beads are washed with chloroform, acetonitrile, and methylene chloride, followed by oxidation for 5 minutes with 1.5 ml of a 0.1 M iodine solution in THF/pyridine/water (40/20/1 by volume). After removal of this solution, the beads are washed with methylene chloride and dried with an argon stream. Concentrated ammonium hydroxide is then added to the beads and they are allowed to stand for 1 hour at room temperature. The ammonium hydroxide solution is then removed and the beads are rinsed with an additional 1 ml of ammonium hydroxide. The combined solution extracts are then stored at 55° C. overnight, followed by lyophilization to isolate the photolabeled oligonucleotide.

We claim:

1. A photoactivatable nucleic acid comprising a nucleic acid having one or more photoreactive groups indirectly bound thereto, wherein the photoreactive groups each generate a active species selected from the group consisting of nitrenes, carbenes, and excited states of ketones upon absorption of electromagnetic energy, and wherein one or more nucleic acids and the one or more photoreactive groups are bound to a common polymeric backbone.

2. A probe array comprising:
   a) a substrate;
   b) a plurality of nucleic acids or derivatives thereof; and
   c) a polymer formed from monomers having a polymerizable vinyl group, wherein at least one monomer has a photoreactive group that is covalently bound to the substrate and wherein the photoreactive group generates an active species selected from the group consisting of nitrenes, carbenes, and excited states of ketones, upon absorption of electromagnetic energy, and wherein at least one monomer has a group reacted with the nucleic acid or derivative thereof for binding the nucleic acid to the polymer.

3. A method comprising the steps of:
   a) derivitizing a monomer having a polymerizable vinyl group with a photoreactive group, wherein the photoreactive group comprises a functional group independently selected from the group consisting of an aryl ketone, an azide, a diazo compound, and a diazirine, thereby forming a photoreactive monomer;
   b) derivitizing a monomer having a polymerizable vinyl group with a group reactive to a nucleic acid or derivative thereof, thereby forming a nucleic acid-reactive monomer;
   c) reacting the nucleic acid-reactive monomer with the nucleic acid or derivative thereof, thereby forming a nucleic acid-coupled monomer; and
   d) copolymerizing the photoreactive monomer and the nucleic acid-coupled monomer to form a photoactivatable nucleic acid.

4. The method according to claim 3 wherein the photoactivatable nucleic acid comprises more than one photoreactive group, and wherein the photoactive groups are identical.

5. The method according to claim 3 wherein the aryl ketone is selected from the group consisting of acetophenone, benzophenone, anthraquinone, and anthrone.

6. The method according to claim 3 wherein the aryl ketone is selected from the group consisting of acridone, xanthone, and thioxanthone.

7. An array comprising a surface and a plurality of nucleic acid compositions covalently attached to the surface, the nucleic acid compositions comprising a polymer formed from monomers having a polymerizable vinyl group, at least one nucleic acid coupled to the polymer, and at least one photoreactive group coupled to the polymer, wherein each of the photoreactive groups comprises a functional group selected from the group consisting of an aryl ketone, an azide, a diazo compound, and a diazirine.

8. The array according to claim 7 wherein each of the nucleic acid compositions comprise more than one photoreactive group, and wherein the photoreactive groups are identical.

9. The array according to claim 7 wherein the aryl ketone is selected from the group consisting of acetophenone, benzophenone, anthraquinone, and anthrone.

10. The array according to claim 7 wherein the aryl ketone is selected from the group consisting of arcridone, xanthone, and thioxanthone.

11. The array according to claim 7 wherein the surface is selected from the group consisting of polypropylene, polystyrene, poly(vinyl chloride), polycarbonate, poly (methyl methacrylate), parylene, and inorganic surfaces pretreated with organosilanes.

12. The array according to claim 7 wherein the nucleic acid compositions are covalently attached to the surface in a specific pattern, and wherein the at least one nucleic acid comprises a synthetic oligonucleotide.

13. A method for immobilizing a nucleic acid on a support comprising steps of:
   a) forming a polymer from monomers having a polymerizable vinyl group, wherein at least one nucleic acid is coupled to the polymer and at least one photoreactive group is coupled to the polymer, each photoreactive group comprising a functional group independently selected from the group consisting of an aryl ketone, an azide, a diazo compound, and a diazirine; and
   b) activating the at least one photoreactive group of the polymer with electromagnetic energy, thereby coupling the polymer to the support.

14. The method according to claim 13 wherein the surface is selected from the group consisting of polypropylene, polystyrene, poly(vinyl chloride), polycarbonate, poly (methyl methacrylate), and inorganic surfaces pretreated with organosilanes or parylene.

15. The method according to claim 13 wherein the support is the surface of a probe array.

16. The probe array according to claim 2 wherein the monomers having a polymerizable vinyl group are selected from the group consisting of acrylamide and derivatives thereof.

17. The probe array according to claim 2 wherein the monomers having a polymerizable vinyl group are selected from the group consisting of malemide and derivatives thereof.

18. The probe array according to claim 2 wherein the monomers consist essentially of n-succinimidyl 6-maleimidohexanoate, 4-benzoyl-N-[3-(2-methyl-acryloylamino)-propyl]-benzamide, and acrylamide.

19. The method of claim 3 wherein the step of copolymerizing further comprises copolymerizing with a non-photoreactive monomer having a polymerizable vinyl group.

20. A method comprising the steps of:
   a) derivitizing a monomer having a polymerizable vinyl group with a photoreactive group, wherein the photoreactive group comprises a functional group independently selected from the group consisting of an aryl ketone, an azide, a diazo compound, and a diazirine, thereby forming a photoreactive monomer;
   b) derivitizing a monomer having a polymerizable vinyl group with a group reactive to a nucleic acid or derivative thereof, thereby forming a nucleic acid-reactive monomer;
   c) copolymerizing the photoreactive monomer and the nucleic acid-reactive monomer to form a nucleic acid-reactive photoactivatable polymer; and
   d) reacting the nucleic acid-reactive photoactivatable polymer with the nucleic acid or derivative thereof, thereby forming a nucleic acid-coupled photoactivatable polymer.

21. The method of claim 20 wherein the step of copolymerizing further comprises copolymerizing with a non-photoreactive monomer having a polymerizable vinyl group.

* * * * *